Figure 1:
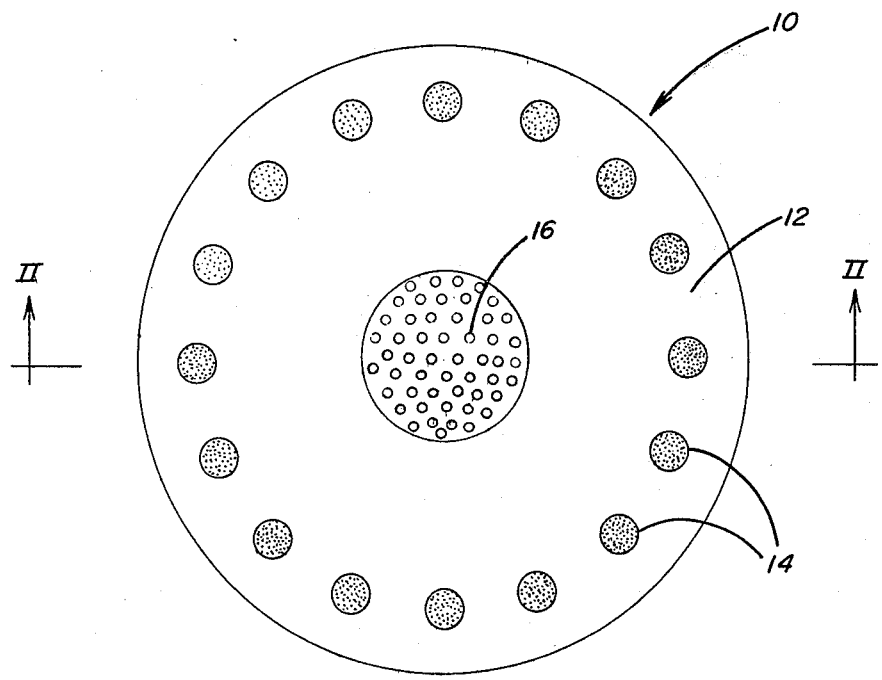

United States Patent [19]

Guistini et al.

[11] 4,381,772
[45] May 3, 1983

[54] BIOERODIBLE DIAPHRAGM

[76] Inventors: Fernando G. Guistini, 22 Boxwood Cir.; Frank J. Keefer, 7 Dawn Ree Acres, both of Wheeling, W. Va. 26003; Robert F. Keefer, 1276 Colonial Dr., Morgantown, W. Va. 26505

[21] Appl. No.: 208,569

[22] Filed: Nov. 20, 1980

[51] Int. Cl.³ .............................................. A61F 5/46
[52] U.S. Cl. ................................ 128/132 R; 424/19; 604/55; 604/890
[58] Field of Search ................... 128/132 R, 127, 130, 128/260, 271; 424/19

[56] References Cited

U.S. PATENT DOCUMENTS

| | | | |
|---|---|---|---|
| 3,143,472 | 8/1964 | Lappas | 167/82 |
| 3,443,563 | 5/1969 | Ishihama | 128/271 |
| 3,763,861 | 10/1973 | Forti | 128/271 |
| 3,811,444 | 5/1974 | Heller | 128/272 |
| 3,888,975 | 6/1975 | Ramwell | 424/15 |
| 3,914,402 | 10/1975 | Shell | 424/32 |
| 3,971,367 | 7/1976 | Zaffaroni | 128/130 |
| 3,986,510 | 10/1976 | Higrichi | 128/260 |
| 4,180,064 | 12/1979 | Heller | 128/130 |

OTHER PUBLICATIONS

Skeist, "Handbook of Adhesives" p. 369, 1964.

*Primary Examiner*—Allan Lieberman
*Assistant Examiner*—Patricia Short
*Attorney, Agent, or Firm*—Stanley J. Price, Jr.; John M. Adams

[57] ABSTRACT

An improved contraceptive diaphragm is provided which has a bioerodible matrix that disintegrates in the vaginal fluids within a predetermined period of time. The matrix is made from a water soluble gel, more particularly from a water soluble polymeric resin gel, and preferably from a polyvinyl alcohol resin gel. The solubility of the water soluble gel in the vaginal fluids is controllably reduced for example, by heat treatment of the gel after formation of the diaphragm. The diaphragm does not have to be removed in a single piece, but is excreted as a slight vaginal discharge. In one aspect of the invention, a natural collagenous protein is embedded in the matrix to assure sealing adherence of the diaphragm when positioned in the vagina. In another aspect of the invention a hydrophilic material is provided at the center of the matrix to effectively absorb secreted cervical mucus thereby creating a dry passageway which will impede entrance of the sperm.

6 Claims, 5 Drawing Figures

BIOERODIBLE DIAPHRAGM

The invention relates to a contraceptive device in the form of a diaphragm capable of bioeroding in the vaginal fluids in a predetermined period of time.

Bioerodible devices exist or have been proposed which dispense active agents to an environment of use in the body at a controlled and continuous rate over a prolonged period of time. An erodible intrauterine device is disclosed in U.S. Pat. No. 3,888,975. The device is of a shape and size adapted for insertion and retention in the uterus and/or cervix uteri. As the polymeric body of the device erodes, it releases the dispersed drug at a controlled rate.

In U.S. Pat. No. 4,180,064, a bioerodible device is disclosed which consists of a drug release rate controlling material comprising a hydrophobic poly (carboxylic acid) having an average of one ionizable hydrogen for each 8 to 22 total carbon atoms. These polyacids erode in response to the environment of use at a controlled and continuous rate by a process of carboxylic hydrogen ionization. Cited examples of use of the device include local delivery of drug to the uterus and vagina.

In U.S. Pat. No. 3,971,367, an intrauterine device is described which releases a therapeutically effective flow of drug to the uterus over a defined dosage period. The device is fabricated to undergo a structural biotransformation during its period in the uterus from an initial uterineretentive configuration to a configuration at the completion of the defined dosage period which is not uterine retentive and which permits the device to be spontaneously eliminated from the uterus.

Bioerodible ocular devices or dosage forms are described in U.S. Pat. Nos. 3,811,444; 3,914,402; and 3,986,510. These provide for the continuous administration of a predetermined, effective dosage of drug to the eye over a prolonged period of time. In the last mentioned patent, the described device bioerodes in the environment of the eye concurrently with the dispensing of the therapeutically desired amount of the drug.

Finally, bioerodible enteric compositions are employed to protect a medicament from undesirable disintegration in the stomach, but release medicament in a desired portion of the intestinal tract as a result of the bioerosion of the enteric coating. Illustrative of the many patents disclosing such enteric compositions is U.S. Pat. No. 3,143,472.

In accordance with the present invention, an improved contraceptive diaphragm is provided which has a bioerodible matrix that disintegrates in the vaginal fluids within a predetermined period of time. The matrix is made from a water-soluble gel, more particularly from a water-soluble polymeric resin gel, and preferably from a polyvinyl alcohol resin gel. The solubility of the water-soluble gel in the vaginal fluids is controllably reduced, for example by means of heat treatment of the gel. If desired, the matrix may also have a spermatocide on its outer surface or dispersed therein.

In an optional aspect of this invention, a collagenous protein is embedded in the peripheral or outer portion of the matrix to assure adherence of the diaphragm to the mucus membrane lining of the vaginal wall close to or on the cervix, to prevent sperm from reaching the cervical canal. This collagenous protein does not dissolve but will be excreted as small particles from the vagina.

In another optional aspect of the present invention, there is provided in the central area of the matrix a mucus-absorbing hydrophilic substance for contact with the cervix to absorb cervical mucus and essentially create a dry area which impedes entrance of sperm, thereby providing further protection.

The term "bioerodible" as used in the specification and claims, is defined as that characteristic of the material used in the matrix which provides desired innocuous disintegration or dissolution of the diaphragm as a unit or entity within the designated desired time period as influenced by the vaginal environment into which it is placed. The products formed by this bioerosion are expelled as a slight vaginal discharge.

The term "predetermined period of time", as used in the specification and appended claims, means the time period following placement of the diaphragm in the vagina which is necessary for the bioerosion to occur as indicated under the definition of the term "bioerodible". Generally, the time period is from 30 minutes to 30 hours, but preferably from 8 to 16 hours.

In the preferred embodiment of the improved diaphragm of this invention, a water-soluble gel composed of a polyvinyl alcohol resin is used to form the matrix. A plasticizer is added in an amount sufficient to provide flexibility of the matrix, and may be, for example, glycerine. A spermatocide, for example, sodium lauryl sulfate, is mixed with the matrix. Pieces of natural collagen are embedded in the matrix in the peripheral portion of the diaphragm facing the cervix, and hydrogel crystals are embedded in the center. The matrix is then dried by heating, e.g. at 105° C. The drying time affects the time required for bioerosion to reach the point of disintegration; the shorter the drying time, the shorter the time required for disintegration to occur. The time for disintegration may be extended by spraying the matrix with dilute solutions of glutaraldehyde, or by adding dilute solutions of acidified formaldehyde to the mixture.

The diaphragms of this invention may assume a great number of variations as to size and shape so long as they are compatible with the objectives as outlined.

Figure 2:
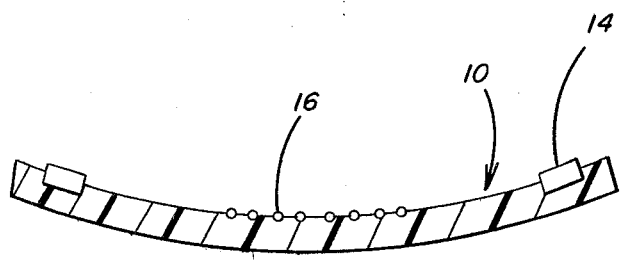
Figure 3:
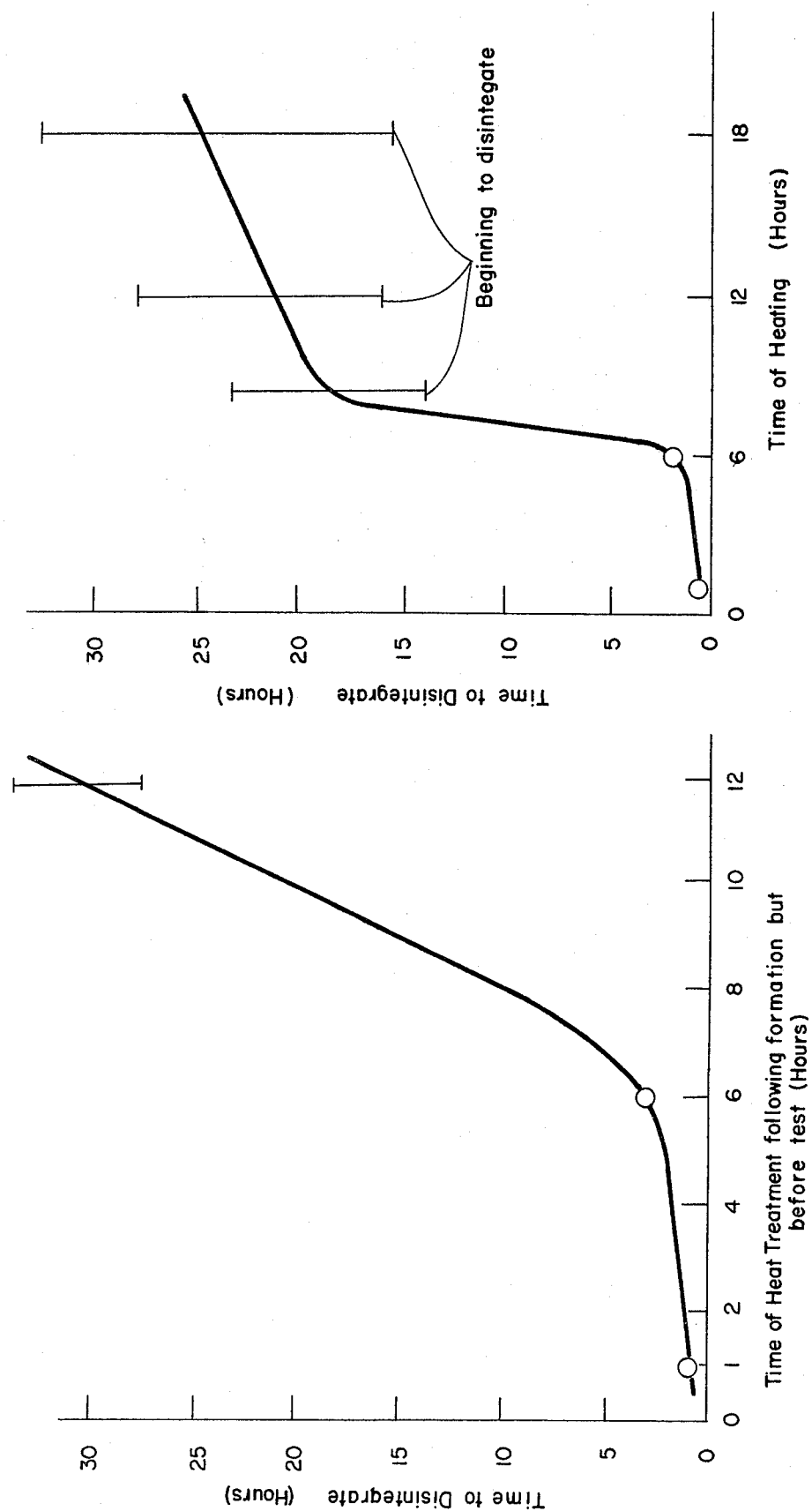
Figure 4:
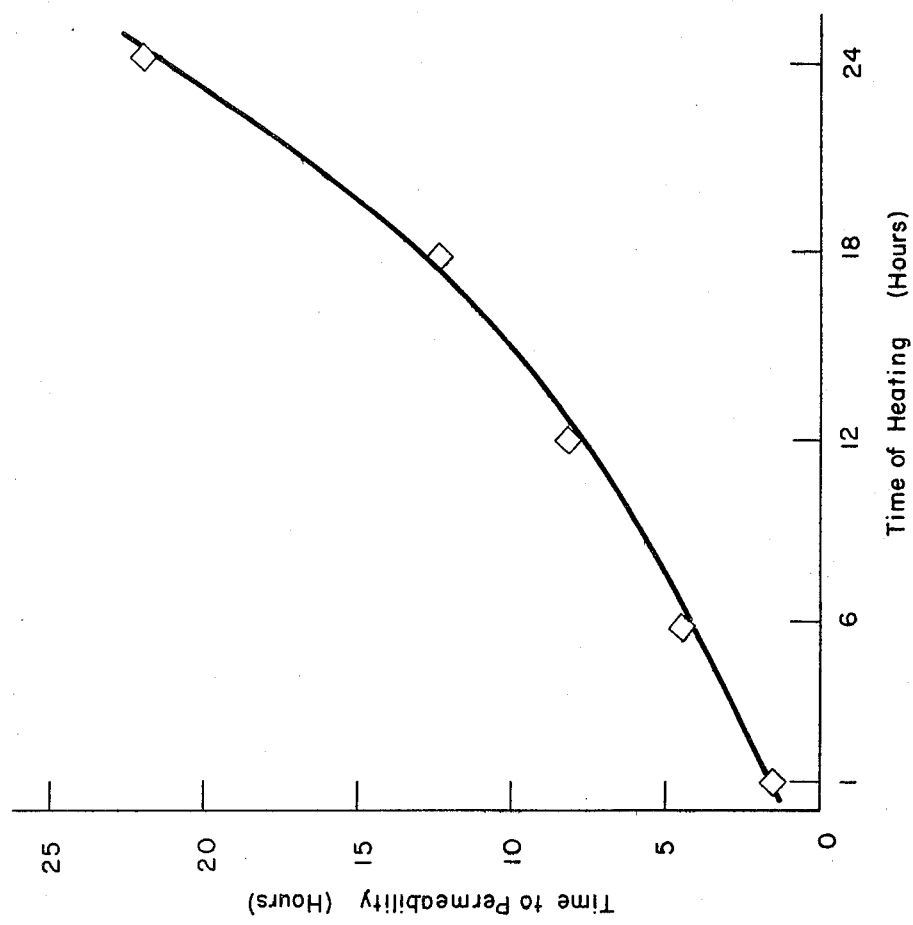

For a better understanding of the present invention, its objects and advantages, reference should be made to the accompanying drawings. FIG. 1 is a top view of a diaphragm embodying a preferred embodiment of this invention and FIG. 2 is a vertical cross-sectional view of the diaphragm shown in FIG. 1, along its diameter. FIG. 3 is a graph of the effect of heating upon the disintegration of a diaphragm of this invention. FIG. 4 is a graph of the effect of heating upon the permeability of a diaphragm having the same composition as that of FIG. 3. FIG. 5 is a graph of the effect of heating upon the disintegration of a diaphragm having a different composition from that of FIG. 3.

Referring to FIGS. 1 and 2 of the drawings, a diaphragm 10 of a conventional shape is shown, and comprises (a) a bioerodible flexible matrix 12 (b) peripherally embedded pieces 14 of a natural collagenous protein, and (c) a moisture-absorbing hydrophilic substance 16 in the center of the diaphragm.

The matrix 12 may be produced using various types of water-soluble gels presently on the market. For this preferred embodiment, "Gelvatol" resins marketed by Monsanto Polymers and Petrochemicals Co., 800 N. Lindberg Blvd., St. Louis, MO 63166, were used. "Gelvatol" resins are polyvinyl alcohol resins which have the characteristics of rapid solubility in water, flexibility, toughness and tenacious adhesion. The resins form non-porous and impermeable membranes or films when cast from water solutions onto level glass or polished metal surfaces. A plasticizer and a spermatocide are mixed together with the resin in the casting water solution of the matrix. Then, before drying, pieces of cut natural collagen are embedded in the matrix, and a hydrophilic material is embedded in the center. The matrix is then dried to form the desired film or membrane.

The plasticizer aids in keeping the matrix flexible. The preferred plasticizer used for polyvinyl alcohol resin is glycerine. Generally, the most effective plasticizers for the "Gelvatol" polyvinyl alcohol resins are those with a chemical structure similar to polyvinyl alcohol. Water soluble organic compounds are generally used.

The water resistance of the water soluble gels is increased by heat treatment of the matrix after formation of the film or membrane. The effects of time of heating upon the disintegration and upon the permeability respectively of a diaphragm of this invention are shown in FIG. 3 and FIG. 4. The diaphragm was made as follows. Three (3) grams of Gelvatol resin 20-90, two (2) grams of Gelvatol resin 20-30 and one (1) gram of sodium lauryl sulfate were mixed dry. Twenty five (25) milliliters (ml.) of water were added to the dry mixture and stirred. Two (2) ml. of glycerine were added. The resulting mixture was further stirred and then poured into a mold to be subjected, after formation of the diaphragm, to heat treatment at 105°, the results of which are graphically depicted in FIGS. 3 and 4. The test for disintegration consisted of immersion of the diaphragm, following the indicated period of heating, in water maintained at body temperature, and observation of the time required for disintegration, as noted visually, to occur. The test for permeability consisted of observing how long it took for water at room temperature to pass vertically through a horizontally suspended diaphragm that had been heated for the period of time indicated on the graph.

FIG. 5 depicts graphically the results obtained from disintegration tests on a diaphragm made as follows. Five (5) grams of Gelvatol resin 20-60 and one (1) gram of sodium lauryl sulfate were mixed dry. A mixture of 25 ml. of water and 2 ml of glycerine was then mixed with the dry mixture and poured into a mold for formation of the diaphragm in conventional manner.

Any conventional spermatocide may be added to the casting solution. The spermatocide is released as the matrix bioerodes.

The pieces 14 of natural collagen which are peripherally embedded in the matrix improve the adhesion of the diaphragm surface to the vaginal walls and to the outer wall of the cervix. These collagenous protein pieces do not need to be round but can be various shapes. They must consist of freeze-dried natural collagen which has been cut across the grain following the freeze-drying process. This cut exposes the collagen fibers and natural small openings. Such open-grained collagen has the unusual property of adhering to mucus membranes that are found in the vagina. Apparently, the capillaries of the collagen act as tiny suction cups. This collagen does not dissolve, but will morselize upon disintegration of the matrix, to provide ease of excretion from the vagina.

For further assurance that sperm does not reach the cervical canal, a hydrophilic material, e.g. hydrogel, is centrally embedded on the side of the diaphragm facing the cervix in the central portion of the matrix 12. The hydrophilic material absorbs the mucus at the cervix, decreasing the effectiveness of the mucus as a sperm transport media. An example of a suitable hydrogel is that sold by Union Carbide Corporation under the trademark "Viterra."

According to the provisions of the Patent Statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A contraceptive vaginal diaphragm composed of a bioerodible matrix which disintegrates in the vaginal fluids within a selected predetermined period of time between 30 minutes to 30 hours, said matrix being made from a water soluble gel.

2. A contraceptive vaginal diaphragm composed of a bioerodible matrix which disintegrates in the vaginal fluids within a selected predetermined period of time between 30 minutes to 30 hours, said matrix being made from a heat treated water soluble gel.

3. A contraceptive vaginal diaphragm composed of a bioerodible matrix which disintegrates in the vaginal fluids within a selected predetermined period of time between 30 minutes to 30 hours, said matrix being made from a water soluble polymeric resin gel.

4. A contraceptive vaginal diaphragm composed of a bioerodible matrix which disintegrates in the vaginal fluids within a selected predetermined period of time between 30 minutes to 30 hours, said matrix being made from a water soluble polyvinyl alcohol resin gel.

5. A contraceptive vaginal diaphragm composed of a bioerodible matrix which disintegrates in the vaginal fluids within a selected predetermined period of time between 30 minutes to 30 hours, said matrix consisting essentially of a heat treated water soluble polyvinyl alcohol resin gel, a plasticizer, and peripherally embedded collagenous particles.

6. A contraceptive vaginal diaphragm composed of a bioerodible matrix which disintegrates in the vaginal fluids within a selected predetermined period of time between 30 minutes to 30 hours, said matrix consisting essentially of a heat treated water soluble polyvinyl alcohol resin gel, a plasticizer, peripherally embedded collagenous particles, centrally embedded hydrophilic crystals and a spermatocide.

* * * * *